(12) United States Patent
Puppala et al.

(10) Patent No.: US 9,062,049 B2
(45) Date of Patent: Jun. 23, 2015

(54) PROCESS FOR THE PREPARATION OF PALIPERIDONE

(75) Inventors: Ravikumar Puppala, Karnataka (IN); Srinivas Laxminarayan Pathi, Karnataka (IN); Rajendra Narayanrao Kankan, Maharashtra (IN)

(73) Assignee: Cipla Limited, Mumbai, IN (US)

( * ) Notice: Subject to any disclaimer, the term of this patent is extended or adjusted under 35 U.S.C. 154(b) by 0 days.

(21) Appl. No.: 14/122,108

(22) PCT Filed: May 30, 2012

(86) PCT No.: PCT/GB2012/000480
§ 371 (c)(1),
(2), (4) Date: Jan. 17, 2014

(87) PCT Pub. No.: WO2012/164242
PCT Pub. Date: Dec. 6, 2012

(65) Prior Publication Data
US 2014/0200228 A1  Jul. 17, 2014

(30) Foreign Application Priority Data
May 30, 2011 (IN) .................. 1592/MUM/2011

(51) Int. Cl.
*C07D 471/04* (2006.01)
(52) U.S. Cl.
CPC .................. *C07D 471/04* (2013.01)
(58) Field of Classification Search
CPC .................................. C07D 487/04
See application file for complete search history.

(56) References Cited

U.S. PATENT DOCUMENTS 5,158,952 A   10/1992  Janssen et al.

FOREIGN PATENT DOCUMENTS

| WO | 2008140641 A2 | 11/2008 |
| WO | 2009118655 A2 | 10/2009 |
| WO | WO2009/144288 | * 12/2009 |
| WO | 2010003702 A1 | 1/2010 |
| WO | 2010003703 A2 | 1/2010 |
| WO | 2010004578 A2 | 1/2010 |
| WO | 2011006638 A1 | 1/2011 |
| WO | 2012164242 A1 | 12/2012 |
| WO | 2012164242 A8 | 12/2012 |

OTHER PUBLICATIONS

Foreign communication from the priority application—International Search Report and Written Opinion, PCT/GB2012/000480, Jul. 30, 2012, 9 pages.
Foreign communication from the priority application—International Preliminary Report on Patentability, PCT/GB2012/000480, Dec. 2, 2013, 7 pages.

* cited by examiner

*Primary Examiner* — Brian McDowell
(74) *Attorney, Agent, or Firm* — Rodney B. Carroll; Conley Rose, P.C.

(57) ABSTRACT

The present invention provides a process for the preparation of paliperidone or a pharmaceutically acceptable salt thereof, wherein the process comprises condensing a compound of formula (II)

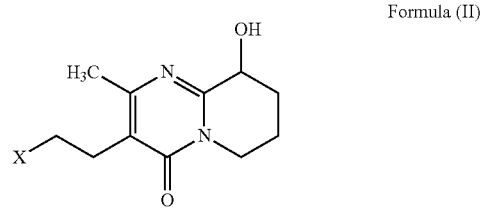

Formula (II)

with a compound of formula (III) or a salt thereof,

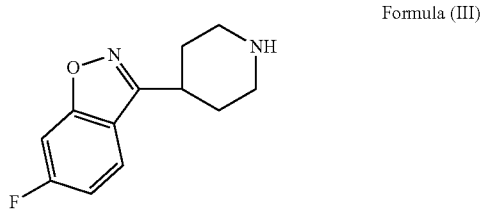

Formula (III)

in a suitable solvent and a base, in the presence of a catalyst and an inhibiting agent, wherein the inhibiting agent is added to the reaction system before the compound of formula (II) and compound of formula (III) have reacted or as the reaction of the compound of formula (II) and compound of formula (III) is initiated, and optionally converting the paliperidone to a salt thereof, wherein X is a suitable leaving group. The present invention also provides substantially pure paliperidone or a salt thereof, paliperidone or a salt thereof as prepared by the process and uses of the paliperidone or salt thereof.

31 Claims, No Drawings

PROCESS FOR THE PREPARATION OF PALIPERIDONE

CROSS-REFERENCE TO RELATED APPLICATIONS

This application is a filing under 35 U.S.C. 371 of International Application No. PCT/GB2012/000480 filed May 30, 2012, entitled "Preparation of Paliperidone," which claims priority to Indian Patent Application No. 1592/MUM/2011 filed May 30, 2011, which applications are incorporated by reference herein in their entirety.

FIELD OF INVENTION

The present invention relates to an improved process for the preparation of paliperidone.

BACKGROUND OF THE INVENTION

Paliperidone is chemically known as 3-[2-[4-(6-Fluoro-1,2-benzisoxazol-3-yl)-1-piperidinyl]ethyl]-6,7,8,9-tetrahydro-9-hydroxy-2-methyl-4H-pyrido[1,2-a]pyrimidin-4-one and represented as follows:

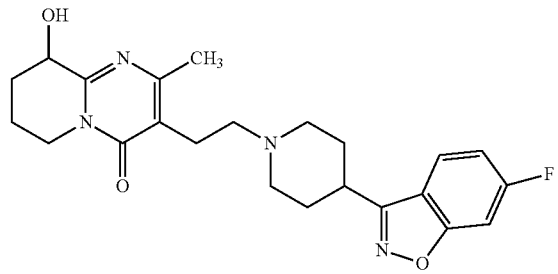 [SMILES: Cc1nc2n(c(=O)c1CCN1CCC(c3noc4cc(F)ccc34)CC1)CCCC2O]

U.S. Pat. No. 5,158,952 describes various processes for the synthesis of paliperidone in which one route involves condensation of 3-(2-chloroethyl)-6,7,8,9-tetrahydro-9-hydroxy-2-methyl-4H-pyrido[1,2-a]pyrimidin-4-one with 6-fluoro-3-(4-piperidinyl)-1,2-benzisoxazole hydrochloride in the presence of a base followed by purification using column chromatography and recrystallization in a suitable solvent. Disadvantages of this process are low yields and purification by column chromatography.

It is known that a drug substance prepared by chemical synthesis usually contains impurities resulting from its synthesis or degradation. These impurities include unreacted starting materials, reagents, by-products of the reaction, products of the side reactions or degradation products.

9-oxo-risperidone (I) is one of the impurities which is formed during the synthesis of paliperidone and which affects the purity of the final product.

This impurity is also known as PLP-ceto or keto impurity. The structure of this impurity is as follows:

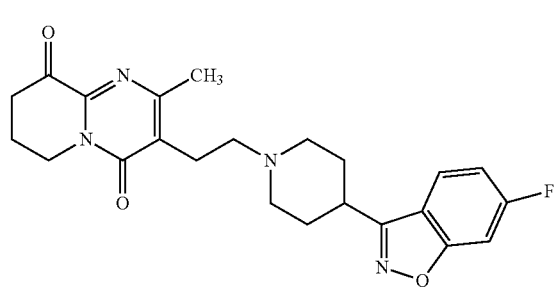

Keto impurity

The undesired impurities reduce the purity of the Active Pharmaceutical Ingredient (API) in the pharmaceutical product and often decrease the stability and shelf life of the pharmaceutical product. Thus, reducing or limiting these undesired impurities becomes very crucial.

The normal techniques of reducing such impurities are known to the skilled person, such as fractional crystallization or preferably by optimizing reaction conditions whereby impurity formation is reduced or avoided. Alternatives, in cases where a product is obtained having related impurities generated in the process of preparation, is to resort to expensive column chromatography or the preparation of derivatives such as salts, esters in order to purify and regenerate the final product in a pure form.

WO2008140641 describes purification of paliperidone by crystallization or by slurrying paliperidone in an organic solvent.

WO2011006638 describes preparation of paliperidone in an organic solvent and in the presence of water wherein the pH of the reaction medium is between 6 and 14. Further, purification of paliperidone is achieved by crystallization in the presence of active charcoal having neutral pH value and the content of individual metal cations less than 200 ppm.

Several attempts have been made to reduce the level of keto impurity, and various patent applications have been filed which describe purification methods to reduce the level of keto impurity in paliperidone. However, these methods are lengthy and tedious, requiring dissolution in a solvent, refluxing for several hours, further isolation and crystallization. The methods are also costly as they involve the use of additional solvents.

WO2009118655 describes purification of crude paliperidone by contacting it with reducing agent. The reducing agents include metal hydrides, specifically sodium borohydride. However, this application involves purification of crude paliperidone by a series of dissolution, filtration and washing steps. The process also requires treatment with activated carbon or silica gel.

WO2010003703 describes preparation, isolation of keto impurity and its further use in the preparation of paliperidone. Keto impurity is converted into paliperidone by reduction using hydride, specifically sodium borohydride.

WO2010004578 discloses various processes for preparation of paliperidone. On page 10, step b), it describes that the paliperidone obtained in the earlier step is treated with sodium borohydride to convert any amount of keto impurity that is formed and present as an impurity, into paliperidone. The process disclosed on page 11 describes that keto impurity is first prepared and then treated with suitable reducing agent, which is sodium borohydride.

Both processes require further stirring of 1 hour after addition of reducing agent, and then an additional one and a half hours for purification and isolation, which is again time consuming.

All the processes described in these prior art applications involve preparation and isolation of paliperidone and/or keto impurity and then treatment with reducing agent, or treating paliperidone and/or keto impurity formed in the reaction with reducing agent, which makes the process lengthy, costly and also affects the yield of the final product.

Since it is difficult to remove the impurities by the above techniques, and the methods known in the art are cumbersome and involve additional steps causing yield loss, there is a need to provide an improved process that is industrially favorable, provides substantially pure paliperidone or a pharmaceutically acceptable salt thereof, and which also provides a better yield of paliperidone.

SUMMARY OF THE INVENTION

According to the first aspect of the present invention, there is provided an improved process for the preparation of paliperidone or a pharmaceutically acceptable salt thereof, in which the formation of keto impurity is inhibited.

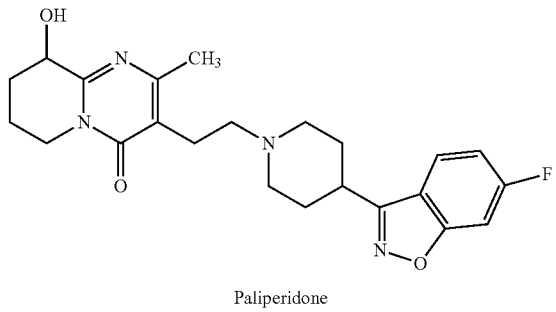 [SMILES: Cc1nc2n(c(=O)c1CCN1CCC(c3noc4cc(F)ccc34)CC1)CCCC2O]

Paliperidone

In an embodiment, the process involves condensing 3-(2-chloroethyl)-9-hydroxy-2-methyl-6,7,8,9-tetrahydro-4H-pyrido-[1,2-a]-pyrimidin-4-one of formula (IIA)

Formula (IIA)

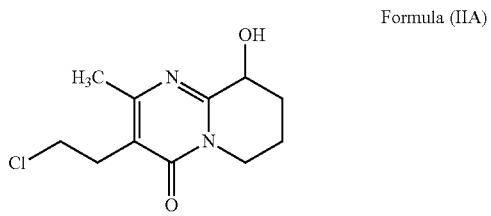 [SMILES: Cc1nc2n(c(=O)c1CCCl)CCCC2O]

with 6-fluoro-3-(4-piperidinyl)-1,2-benzisoxazole hydrochloride of formula (III)

Formula (III)

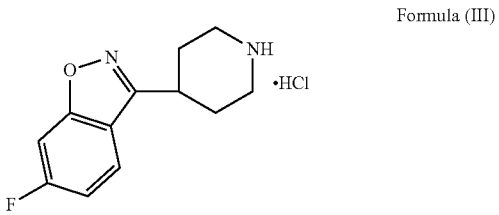 [SMILES: Fc1ccc2c(C3CCNCC3)noc2c1 ; Cl]

in a suitable solvent and a base, in the presence of a catalyst and a catalytic amount of inhibiting agent to obtain paliperidone or a pharmaceutically acceptable salt thereof.

According to a second aspect of the present invention, there is provided a process for the preparation of paliperidone or a pharmaceutically acceptable salt thereof, wherein the process comprises condensing a compound of formula (II)

Formula (II)

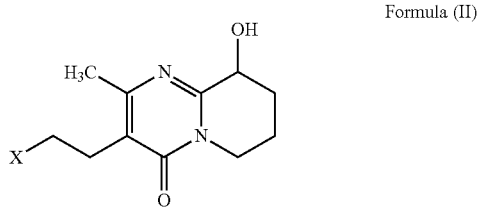

with a compound of formula (III) or a salt thereof,

Formula (III)

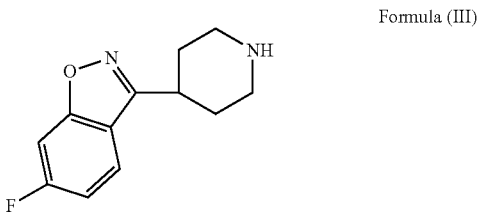 [SMILES: Fc1ccc2c(C3CCNCC3)noc2c1]

in a suitable solvent and a base, in the presence of a catalyst and an inhibiting agent, wherein the inhibiting agent is added to the reaction system before the compound of formula (II) and compound of formula (III) have reacted or as the reaction of the compound of formula (II) and compound of formula (III) is initiated, and optionally converting the paliperidone to a salt thereof, wherein X is a suitable leaving group.

As noted above, the inhibiting agent is added to the reaction system before the compound of formula (II) and compound of formula (III) have reacted or as the reaction of the compound of formula (II) and compound of formula (III) is initiated. In other words, the process avoids a reaction sequence in which inhibiting agent is added after compound of formula (II) and compound of formula (III) have reacted and keto impurity has formed.

Preferably, the compound of formula (III) is in the form of a salt. Preferably, the salt of the compound of formula (III) is the HCl salt or the HBr salt. More preferably the salt of the compound of formula (III) is the HCl salt.

X is preferably a halide selected from fluoride, chloride, bromide or iodide. Most preferably X is chloride.

Preferably the inhibiting agent is present in a catalytic amount.

Preferably the inhibiting agent is present in an amount of 0.01 to 0.2 moles per 1 mole of compound of formula (II). More preferably the inhibiting agent is present in an amount of 0.01 to 0.1 moles per 1 mole of compound of formula (II).

Preferably the inhibiting agent is selected from the group consisting of sodium borohydride, potassium borohydride, sodium triacetoxy borohydride, hydrazine hydrate, aluminium isopropoxide, lithium borohydride, diisobutylaluminium hydride, butylated hydroxytoluene, propylgallate, butylhydroxy anisole, tertiary butyl hydro quinine, sodium hydride, sodium meta bisulphite, sodium thio sulphate, and mixtures thereof.

Most preferably the inhibiting agent is selected from sodium borohydride or butylated hydroxytoluene.

Preferably the inhibiting agent comprises sodium borohydride in an amount of 0.01 to 0.2 moles per 1 mole of compound of formula (II), more preferably the inhibiting agent comprises sodium borohydride in an amount of 0.06 moles per 1 mole of compound of formula (II).

Alternatively the inhibiting agent comprises butylated hydroxytoluene in an amount of 0.01 to 0.06 moles of per 1 mole of compound of formula (II), more preferably the inhibiting agent comprises butylated hydroxytoluene in an amount of 0.011 moles per 1 mole of compound of formula (II).

Preferably the catalyst is selected from the group consisting of potassium iodide, sodium iodide, lithium iodide, and mixtures thereof.

More preferably the catalyst is potassium iodide.

Preferably the base is selected from the group consisting of potassium carbonate, sodium carbonate, cesium carbonate, potassium bicarbonate, sodium bicarbonate, sodium hydroxide, potassium hydroxide, and mixtures thereof.

More preferably the base is potassium carbonate.

Preferably the solvent is selected from the group consisting of methanol, toluene, ethyl acetate, acetonitrile, cyclohexane, dimethyl formamide (DMF), dimethylamine (DMA), dimethyl sulfoxide (DMSO), and mixtures thereof.

More preferably the solvent is acetonitrile.

Preferably the reaction mixture is heated to a temperature range of from 40-80° C., more preferably a temperature range of from 50-70° C., more preferably a temperature range of from 62-68° C.

In an embodiment, the process of the second aspect of the present invention results in paliperidone in free base form. The free base may be converted to a pharmaceutically acceptable salt thereof.

In all aspects of the present invention in which paliperidone is optionally converted to a salt thereof, the salt is an acid addition salt formed by treatment with an appropriate acid, such as a hydrohalic acid, for example hydrochloric or hydrobromic acid, sulfuric acid, nitric acid, phosphoric acid, acetic acid, propanoic acid, hydroxyacetic acid, 2-hydroxypropanoic acid, 2-oxopropanoic acid, ethanedioic acid, propanedioic acid, butanedioic acid, (Z)-2-butenedioic acid, (E)-2-butenedioic acid, 2-hydroxybutanedioic acid, 2,3-dihydroxybutanedioic acid, 2-hydroxy-1,2,3-propanetricarboxylic acid, methanesulfonic acid, ethanesulfonic acid, benzenesulfonic acid, 4-methylbenzenesulfonic acid, cyclohexanesulfamic acid, 2-hydroxybenzoic acid or 4-amino-2-hydroxybenzoic acid.

Preferably the paliperidone prepared by the process according to the second aspect of the invention is converted to a salt, most preferably the HCl salt.

According to a third aspect of the present invention there is provided paliperidone or a pharmaceutically acceptable salt thereof prepared according to the process of the second aspect of the invention.

Optionally, the paliperidone prepared according to the process of the second aspect of the invention may be further purified.

The purification may comprise:
(i) dissolving the paliperidone prepared according to the process of the second aspect of the invention in a chlorinated solvent;
(ii) concentrating the solution; and
(iii) isolating the paliperidone using a suitable solvent.

Preferably step (i) comprises heating the reaction mixture.

Preferably step (ii) comprises heating, distillation and cooling.

Preferably step (iii) comprises filtering, washing and drying under vacuum.

Preferably the chlorinated solvent used in step (i) is selected from the group consisting of methylene chloride, ethylene chloride, chloroform, or mixtures thereof.

More preferably the chlorinated solvent is methylene chloride.

Preferably the chlorinated solvent in step (i) is mixed with a second solvent.

Preferably the second solvent is selected from the group consisting of methanol, isopropyl alcohol, acetone, methyl isobutyl ketone, ethyl acetate, isopropyl acetate, toluene and acetonitrile, or mixtures thereof. Most preferably the second solvent is methanol.

Preferably the suitable solvent used in step (iii) is selected from the group consisting of acetone, methanol, ethyl acetate, isopropyl alcohol, methyl isobutyl ketone (MIBK), acetonitrile, isopropyl acetate, toluene or mixtures thereof.

More preferably the suitable solvent used in step (iii) is methanol.

Preferably the second solvent used in step (i) is the same as the suitable solvent used in step (iii).

According to a fourth aspect of the present invention, there is provided substantially pure paliperidone or a pharmaceutically acceptable salt thereof.

Preferably the substantially pure paliperidone or a pharmaceutically acceptable salt thereof has a keto impurity of 0.06% or less, preferably 0.05% or less, more preferably 0.04% or less, more preferably 0.03% or less, most preferably 0.02% or less.

Preferably the substantially pure paliperidone or a pharmaceutically acceptable salt thereof has a keto impurity of 0.06% or less observed at 25° C. after 12 months.

Preferably the substantially pure paliperidone or a pharmaceutically acceptable salt thereof has a total impurity level of 0.22% or less, more preferably 0.2% or less, more preferably 0.18% or less.

Preferably the substantially pure paliperidone or a pharmaceutically acceptable salt thereof has a total impurity level of 0.22% or less observed at 40° C. after 6 months.

According to a fifth aspect of the present invention, there is provided a pharmaceutical composition comprising paliperidone or a pharmaceutically acceptable salt thereof prepared as described above, together with one or more pharmaceutically acceptable excipients. Such excipients will be well known to those skilled in the art. Further, processes for formulating the pharmaceutical compositions will be well known to those skilled in the art.

In an embodiment, the paliperidone or salt thereof is present in the pharmaceutical composition in combination with another active pharmaceutical ingredient. Suitable active pharmaceutical ingredients for combination with paliperidone would be known to those of skill in the art.

According to a sixth aspect of the present invention, there is provided a pharmaceutical composition comprising substantially pure paliperidone or a pharmaceutically acceptable salt thereof as described above in the fourth aspect, together with one or more pharmaceutically acceptable excipients. Such excipients will be well known to those skilled in the art. Further, processes for formulating the pharmaceutical compositions will be well known to those skilled in the art.

In an embodiment, the substantially pure paliperidone or salt thereof is present in the pharmaceutical composition in combination with another active pharmaceutical ingredient. Suitable active pharmaceutical ingredients for combination with substantially pure paliperidone would be known to those of skill in the art.

According to a seventh aspect of the present invention, there is provided the use of paliperidone or a salt thereof prepared according to any one of the processes described above in medicine. According to an eighth aspect of the present invention, there is provided the use of paliperidone or a salt thereof prepared according to any one of the processes described above in the treatment of schizophrenia or bipolar disorder. According to a ninth aspect of the present invention, there is provided a method of treating schizophrenia or bipolar disorder comprising administering to a patient in need thereof a therapeutically effective amount of paliperidone or a salt thereof prepared according to any one of the processes described above.

DETAILED DESCRIPTION OF THE INVENTION

The present invention relates to an improved process for the preparation of substantially pure paliperidone or a pharmaceutically acceptable salt thereof, in which the formation of keto impurity is inhibited.

The prior art processes involve treatment of paliperidone with reducing agent after completion of the reaction and formation of keto impurity. However, it has been found that if an inhibiting agent is added at the beginning along with the reactants before the formation of paliperidone, that is at the stage of condensation of the reactants, the formation of keto impurity is inhibited.

An "inhibiting agent" for the purposes of this application may be defined as a chemical reagent that inhibits the formation of keto impurity in a process for the preparation of paliperidone. Suitably, the inhibiting agent is a reducing agent or an antioxidant.

In a preferred embodiment the process for preparation of paliperidone involves the step of condensing 3-(2-chloroethyl)-9-hydroxy-2-methyl-6,7,8,9-tetrahydro-4H-pyrido-[1,2-a]-pyrimidin-4-one of formula (IIA)

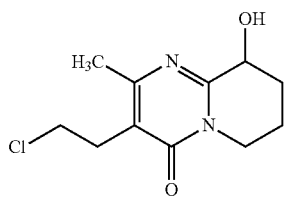

Formula (IIA)

with 6-fluoro-3-(4-piperidinyl)-1,2-benzisoxazole hydrochloride of formula (III)

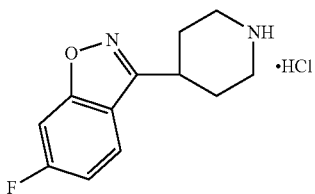

Formula (III)

in a suitable solvent and a base, in the presence of a catalyst.

In an embodiment a catalytic amount of inhibiting agent is added at the same time as the reaction is initiated.

According to an aspect of the present invention, there is provided a process for the preparation of paliperidone or a pharmaceutically acceptable salt thereof, wherein the process comprises condensing a compound of formula (II)

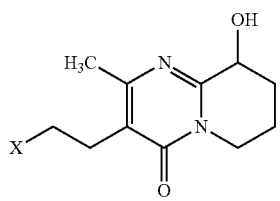

Formula (II)

with a compound of formula (III) or a salt thereof,

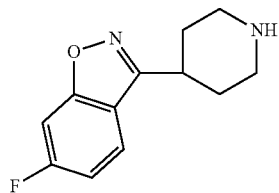

Formula (III)

in a suitable solvent and a base, in the presence of a catalyst and an inhibiting agent, preferably in a catalytic amount, wherein the inhibiting agent is added to the reaction system before the compound of formula (II) and compound of formula (III) have reacted or as the reaction of the compound of formula (II) and compound of formula (III) is initiated, and optionally converting the paliperidone to a salt thereof, wherein X is a suitable leaving group, such as a halide selected from fluoride, chloride, bromide or iodide. It is most preferred that X is chloride.

The compound of formula (III) is preferably in salt form, such as the HCl salt or the HBr salt.

The process of the present invention prevents the oxidation of secondary alcohol and formation of keto impurity. This is achieved by adding the inhibiting agent along with the reactants before the formation of paliperidone, wherein it was observed that the formation of keto impurity was inhibited.

Inhibition of the formation of keto impurity in accordance with the process for preparing paliperidone of the present invention gives rise to numerous advantages. Such advantages may include reducing reaction time, reducing the number of steps of the process, improved industrial feasibility, increasing the yield of paliperidone, increasing the purity of paliperidone obtained by the process and thereby avoiding the requirement for further purification, avoiding the requirement for treatment with activated carbon or silica gel.

Suitable solvents that may be used for the reaction include methanol, toluene, ethyl acetate, acetonitrile, cyclohexane, dimethyl formamide (DMF), dimethylamine (DMA), dimethyl sulfoxide (DMSO), and mixtures thereof, preferably acetonitrile.

The base may be selected from potassium carbonate, sodium carbonate, cesium carbonate, potassium bicarbonate, sodium bicarbonate, sodium hydroxide, potassium hydroxide, and mixtures thereof, preferably potassium carbonate.

The catalyst may be selected from potassium iodide, sodium iodide, lithium iodide, and mixtures thereof, preferably potassium iodide.

The inhibiting agent may be selected from sodium borohydride, potassium borohydride, sodium triacetoxy borohydride, hydrazine hydrate, aluminium isopropoxide, lithium borohydride, diisobutylaluminium hydride, butylated hydroxytoluene, propylgallate, butylhydroxy anisole, tertiary butyl hydro quinine, sodium hydride, sodium meta bisulphite, sodium thio sulphate, preferably sodium borohydride or butylated hydroxytoluene, most preferably sodium borohydride.

The catalytic amount may be achieved by using, for example, 0.01 to 0.2 moles of sodium borohydride per 1 mole of compound of formula (II), preferably 0.06 moles of sodium borohydride per 1 mole of compound of formula (II) or by using, for example, 0.01 to 0.06 moles of butylated hydroxytoluene per 1 mole of compound of formula (II), preferably 0.011 moles of butylated hydroxytoluene per 1 mole of compound of formula (II).

The reaction mixture may be heated to a temperature range of from 40-80° C., preferably a temperature range of from 50-70° C., more preferably a temperature range of from 62-68° C.

The starting materials are known and can be prepared according to processes described in the prior art.

The process described above results in paliperidone in free base form. The free base may be converted to a pharmaceutically acceptable salt thereof. Where paliperidone is converted to a salt thereof, the salt is an acid addition salt formed by treatment with an appropriate acid, such as a hydrohalic acid, for example hydrochloric or hydrobromic acid, sulfuric acid, nitric acid, phosphoric acid, acetic acid, propanoic acid, hydroxyacetic acid, 2-hydroxypropanoic acid, 2-oxopropanoic acid, ethanedioic acid, propanedioic acid, butanedioic acid, (Z)-2-butenedioic acid, (E)-2-butenedioic acid, 2-hydroxybutanedioic acid, 2,3-dihydroxybutanedioic acid, 2-hydroxy-1,2,3-propanetricarboxylic acid, methanesulfonic acid, ethanesulfonic acid, benzenesulfonic acid, 4-methylbenzenesulfonic acid, cyclohexanesulfamic acid, 2-hydroxybenzoic acid or 4-amino-2-hydroxybenzoic acid. It is preferred that the paliperidone is converted to the HCl salt.

The product obtained may optionally be further purified, if required.

The paliperidone obtained by the process of the present invention may be purified by dissolving the paliperidone in a chlorinated solvent, such as methylene chloride, ethylene chloride, chloroform, preferably methylene chloride, and heating the reaction mixture. The chlorinated solvent may be mixed with a second solvent, such as methanol. The solution of paliperidone may then be concentrated by heating, distilling and the then cooling the reaction mixture. The pure paliperidone is then isolated using a suitable solvent, such as acetone, methanol, ethyl acetate, isopropyl alcohol, methyl isobutyl ketone (MIBK), acetonitrile, isopropyl acetate, toluene, preferably methanol. The isolation step comprises filtering the product, washing the product in the suitable solvent, and then drying under vacuum.

Preferably the second solvent with which the chlorinated solvent is mixed is the same as the suitable solvent used in the isolation step.

In another aspect of the present invention, there is provided substantially pure paliperidone or a pharmaceutically acceptable salt thereof.

"Substantially pure paliperidone or a pharmaceutically acceptable salt thereof" may be defined as paliperidone or a pharmaceutically acceptable salt thereof having keto impurity of 0.06% or less, preferably 0.05% or less, more preferably 0.04% or less, more preferably 0.03% or less, most preferably 0.02% or less.

Preferably the substantially pure paliperidone or a pharmaceutically acceptable salt thereof has a keto impurity of 0.06% or less observed at 25° C. after 12 months.

In a preferred embodiment the substantially paliperidone or a pharmaceutically acceptable salt thereof has a total impurity of 0.22% or less, more preferably 0.2% or less, more preferably 0.18% or less.

Preferably the substantially pure paliperidone or a pharmaceutically acceptable salt thereof has a total impurity level of 0.22% or less observed at 40° C. after 6 months.

The substantially pure paliperidone or a pharmaceutically acceptable salt thereof may be in crude form, or alternatively may be further purified. When in crude form, the substantially pure paliperidone may have a keto impurity of 0.06% or less, preferably 0.05% or less, more preferably 0.04% or less, more preferably 0.03% or less, most preferably 0.02% or less. However, in order to have a total impurity of 0.22% or less, more preferably 0.2% or less, or more preferably 0.18% or less, further purification of the crude form of the substantially pure paliperidone or a pharmaceutically acceptable salt thereof may be required.

Paliperidone prepared in accordance with the present invention as described above may be used in the preparation of a pharmaceutical composition comprising paliperidone or a pharmaceutically acceptable salt thereof, together with one or more pharmaceutically acceptable excipients. Such excipients will be well known to those skilled in the art. Further, processes for formulating the pharmaceutical compositions will be well known to those skilled in the art.

The paliperidone or salt thereof may be present in the pharmaceutical composition in combination with another active pharmaceutical ingredient. Suitable active pharmaceutical ingredients for combination with paliperidone would be known to those of skill in the art.

Paliperidone or a salt thereof prepared according to any one of the processes described above may be used in medicine. In particular, paliperidone or a salt thereof prepared according to any one of the processes described above may be used in the treatment of schizophrenia or bipolar disorder. According to an aspect of the present invention, there is provided a method of treating schizophrenia or bipolar disorder comprising administering to a patient in need thereof a therapeutically effective amount of paliperidone or a salt thereof prepared according to any one of the processes described above.

The details of the invention are given in the examples which are provided below for illustration only and therefore these examples should not be construed to limit the scope of the invention.

EXAMPLES

Comparative Example 1

The example 6 of WO 2010/004578 was repeated.

To a solution of 6-fluoro-3-(piperidin-4-yl)benzo[d]isoxazole (10.0 grams) in methanol (50 ml), 3-(2-chloroethyl)-9-hydroxy-2-methyl-6,7,8,9-tetrahydro-4H-pyrido[1,2-a]pyrimidin-4-one (11 grams) and diisopropyl ethyl amine (9 grams) were added. The reaction mixture heated to 65-70° C. and stirred for 24 hours at the same temperature. The reaction mixture was cooled. Dichloromethane (100 ml) and sodium borohydride (0.086 grams) were added to it and stirred for 60 minutes at the same temperature. The solvent was distilled off under reduced temperature. Methanol was added to the residue and heated to reflux for 30 minutes. The reaction mixture was cooled to 20° C. and stirred for 1 hour. Filtered the solid and precipitated. Washed the solid with chilled methanol and dried the compound.

The reducing agent, sodium borohydride, was added to the reaction mass after formation of paliperidone but without isolation of paliperidone, and the formation of keto impurity was monitored at 5 hour intervals.

It was observed that the keto impurity was 1.04% at the end of the reaction before addition of reducing agent. After addition of reducing agent the keto impurity of the reaction mass was reduced to 0.09%, and after isolation of crude paliperidone from the reaction mass the paliperidone contained 0.07% of the keto impurity.

This process requires further stirring of 1 hour after addition of reducing agent and then an additional one and half hours for purification and isolation.

The process of the present invention, on the other hand, avoids the additional steps of (i) isolation of paliperidone or keto impurity and (ii) further treatment with reducing agent, since the inhibiting agent is added initially along with the reactants. Thus, making the process industrially more feasible and also providing better yield.

Comparative Example 2

The process for preparing paliperidone was carried out in accordance with below Example 2, but without the addition of an inhibiting agent and the formation of keto impurity was monitored at 5 hour intervals. It was observed that at the end of the reaction the keto impurity was present in an amount of 1.06%.

Example 1

Preparation of Paliperidone

The process was then carried out with the addition of a catalytic amount of inhibiting agent along with the reactants in accordance with the present invention. The process was carried out in accordance with below Example 2. The formation of keto impurity was monitored at 5 hour intervals. The keto impurity was found to be 0.01% at the end of the reaction.

All impurity measurements in Comparative Example 1, Comparative Example 2 and Example 1 were measured by HPLC.

These results indicate that when an inhibiting agent is added initially along with the reactants before preparation of paliperidone, the formation of keto impurity is hindered and thus impurity is limited to a much lower level than where the addition of the inhibiting agent occurs after the formation of paliperidone.

The results of the above experiments are given in Table 1:

TABLE 1

Paliperidone Keto impurity levels monitored by following example 6 of WO2010004578, process of the present invention without addition of inhibiting agent & the process of the present invention

| Hours | Process of the present invention (Example 1) (%) | Process of the present invention without addition of inhibiting agent (Comparative Example 2) (%) | Example 6 of WO2010004578 (Comparative Example 1) (%) | Remarks |
|---|---|---|---|---|
| 5th Hour | 0.02 | 0.5 | 0.12 | |
| 10th Hour | 0.03 | 0.67 | 0.16 | |
| 15th Hour | 0.03 | 0.82 | 0.43 | |
| 20th Hour | 0.03 | 0.94 | 0.65 | |
| 25th Hour | 0.03 | 1.06 | 1.04 | |
| 26th Hour | — | — | 0.09 | Added sodium borohydride and maintained for 1 hour (for comp. example 1) |
| After isolation | 0.01 | 0.5 | 0.07 | |

Further, the yield of the crude product obtained by following example 6 of the WO2010004578 is 111% w/w while the yield obtained by the process of the present invention is 150% w/w.

The above results indicate that the process of the present invention is improved over the prior art and well suited for industrial scale up.

Example 2

Preparation of Paliperidone 300 ml of acetonitrile was charged followed by 20.0 g of 3-(2-chloroethyl)-9-hydroxy-2-methyl-6,7,8,9-tetrahydro-4H-pyrido-[1,2-a]-pyrimidin-4-one and 21.0 g of 6-fluoro-3-(4-piperidinyl)-1,2-benzisoxazole hydrochloride at room temperature. The reaction mass was stirred at room temperature for 5 minutes and 20.0 g of potassium carbonate and 0.7 g of potassium iodide were charged. Further, 0.2 g of sodium borohydride was charged and the temperature was raised to 65±2° C. The reaction mass was maintained at 65±2° C. for 25 hours. After reaction completion, the reaction mass was slowly cooled to room temperature. The solids were filtered, washed with 50 ml of acetonitrile and then dissolved in 800 ml of methylene chloride at room temperature. The contents were heated to 30-35° C., maintained for 10 minutes, filtered and washed with 20 ml of methylene chloride. The clear filtrate was distilled completely under vacuum below 35° C. and replaced with 50 ml of acetone. Further, 300 ml of acetone was charged, heated to 45° C. and stirred for 30 minutes. The reaction mass was cooled to room temperature and stirred for 1 hour. The product was filtered, washed with 20 ml of acetone and dried under vacuum at 50-55° C. to yield paliperidone (30 g, yield: 150% w/w, efficiency: 85.11%, keto impurity by HPLC: 0.01%, total impurity level by HPLC: 1.0%)

Example 3

Preparation of Paliperidone 300 ml of acetonitrile was charged followed by 20.0 g of 3-(2-chloroethyl)-9-hydroxy-2-methyl-6,7,8,9-tetrahydro-4H-pyrido-[1,2-a]-pyrimidin-4-one and 21.0 g of 6-fluoro-3-(4-piperidinyl)-1,2-benzisoxazole hydrochloride at room temperature. The reaction mass was stirred for 5 minutes and 20.0 g of potassium carbonate and 0.7 g of potassium iodide were charged. Further, 0.2 g of butylated hydroxytoluene was charged and the temperature was raised to 65±2° C. The reaction mass was maintained at 65±2° C. for 25 hours. After reaction completion, the reaction mass was slowly cooled to room temperature. The solids were filtered, washed with 50 ml of acetonitrile and then dissolved in 800 ml of methylene chloride at room temperature. The contents were heated to 30-35° C., maintained for 10 minutes at 30-35° C., filtered and washed with 20 ml of methylene chloride. The clear filtrate was distilled completely under vacuum below 35° C. and replaced with 50 ml of acetone. Further, 300 ml of acetone was charged, heated to 45° C. and stirred for 30 minutes. The reaction mass was cooled to room temperature and stirred for 1 hour. The product was filtered, washed with 20 ml of acetone and dried under vacuum at 50-55° C. to yield paliperidone (27 g, yield: 135% w/w, efficiency: 76.6%, keto impurity by HPLC: 0.03%, total impurity level by HPLC: 1.0%)

Example 4

Purification of Paliperidone 30 g of crude paliperidone was charged in a reaction flask along with 240 ml of methylene chloride and 360 ml of methanol at room temperature. The reaction mixture was heated to 35 to 40° C. and stirred for 20 minutes. Methylene chloride was distilled off completely by 55° C., the contents were cooled to room temperature and stirred for 1 hour. The obtained product was filtered and washed with methanol and dried under vacuum to obtain 26 g of pure paliperidone. Total impurity level by HPLC: 0.17%.

Example 5

Preparation of Salt of Paliperidone 125.0 ml methanol and 25.0 grams g of paliperidone were charged into round bottom flask. The pH of the reaction mixture was adjusted to 2.0 to 3.0 with IPA.HCl. The reaction mixture was stirred, cooled, filtered and dried under vacuum to obtain paliperidone hydrochloride. Dry wt 25.0 grams.

Example 6

Stability of Paliperidone

Paliperidone was prepared as in above Example 2 in accordance with the present invention. The stability of the paliperidone prepared in accordance with the present invention was tested and the results obtained are set out in Table 2. The impurity levels were measured by HPLC.

TABLE 2

|  | Batch 1 | | | Batch 2 | | | Batch 3 | | |
| Impurity data | 25° C. | 30° C. | 40° C. | 25° C. | 30° C. | 40° C. | 25° C. | 30° C. | 40° C. |
| --- | --- | --- | --- | --- | --- | --- | --- | --- | --- |
| Keto impurity | | | | | | | | | |
| Time interval - Initial | 0.02 | 0.02 | 0.02 | 0.03 | 0.03 | 0.03 | 0.04 | 0.04 | 0.04 |
| 1 month | — | 0.03 | 0.03 | — | 0.03 | 0.03 | — | 0.05 | 0.05 |
| 2 months | — | 0.03 | 0.03 | — | 0.03 | 0.03 | — | 0.05 | 0.05 |
| 3 months | 0.02 | 0.03 | 0.03 | 0.02 | 0.03 | 0.03 | 0.04 | 0.04 | 0.05 |
| 6 months | 0.06 | 0.04 | 0.05 | 0.04 | 0.05 | 0.03 | 0.05 | 0.06 | 0.05 |
| 12 months | 0.04 | — | — | 0.05 | — | — | 0.06 | — | — |
| Total impurities | | | | | | | | | |
| Time interval - Initial | 0.17 | 0.17 | 0.17 | 0.17 | 0.17 | 0.17 | 0.20 | 0.20 | 0.20 |
| 1 month | — | 0.19 | 0.20 | — | 0.19 | 0.20 | — | 0.20 | 0.21 |
| 2 months | — | 0.18 | 0.20 | — | 0.20 | 0.20 | — | 0.21 | 0.21 |
| 3 months | 0.15 | 0.16 | 0.17 | 0.16 | 0.18 | 0.18 | 0.20 | 0.21 | 0.21 |
| 6 months | 0.20 | 0.19 | 0.20 | 0.17 | 0.21 | 0.18 | 0.20 | 0.22 | 0.22 |
| 12 months | 0.21 | — | — | 0.20 | — | — | 0.21 | — | — |

The above data shows that paliperidone prepared in accordance with the present invention remains substantially pure over time and elevated temperature and so is highly advantageous in terms of shelf life.

It will be appreciated that the invention may be modified within the scope of the appended claims.

The invention claimed is:

1. A process for the preparation of paliperidone:

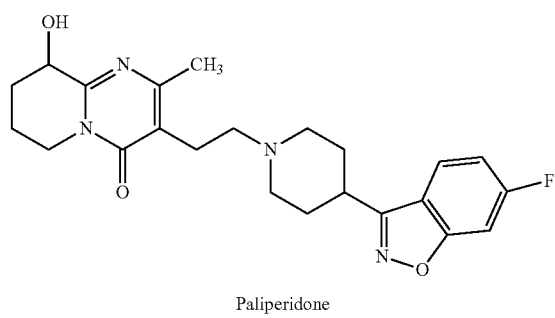 [SMILES: Cc1nc2n(c(=O)c1CCN1CCC(c3noc4cc(F)ccc34)CC1)CCCC2O]

Paliperidone or a pharmaceutically acceptable salt thereof, wherein the process comprises condensing a compound of formula (II)

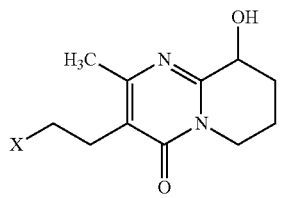

Formula (II)

with a compound of formula (III) or a salt thereof,

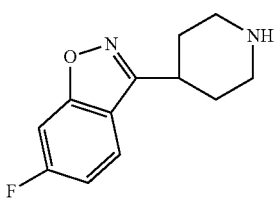

Formula (III)

in a suitable solvent and a base, in the presence of a catalyst and an inhibiting agent, wherein the inhibiting agent is added to a mixture comprising the compound of formula (II) and compound of formula (III) before heating the mixture comprising the compound of formula (II) and the compound of formula (III), and optionally converting the paliperidone to a salt thereof, wherein X is a suitable leaving group.

2. The process according to claim 1 wherein the compound of formula (III) is in the form of a salt.

3. The process according to claim 2 wherein the salt of the compound of formula (III) is the HCl salt or the HBr salt.

4. The process according to claim 1 wherein X is a halide selected from fluoride, chloride, bromide or iodide.

5. The process according to claim 1 wherein the inhibiting agent is present in a catalytic amount.

6. The process according to claim 1 wherein the inhibiting agent is present in an amount of 0.01 to 0.1 moles per 1 mole of compound of formula (II).

7. The process according to claim 1 wherein the inhibiting agent is selected from the group consisting of sodium borohydride, potassium borohydride, sodium triacetoxy borohydride, hydrazine hydrate, aluminium isopropoxide, lithium borohydride, diisobutylaluminium hydride, butylated hydroxytoluene, propygallate, butylhydroxy anisole, tertiary butyl hydro quinine, sodium hydride, sodium meta bisulphate, sodium thio sulphate, and mixtures thereof.

8. The process according to claim 1 wherein the inhibiting agent comprises sodium borohydride in an amount of 0.01 to 0.2 moles per 1 mole of compound of formula (II).

9. The process according claim 1 wherein the inhibiting agent comprises butylated hydroxytoluene in an amount of 0.01 to 0.06 moles of per 1 mole of compound of formula (II).

10. The process according to claim 1 wherein the catalyst is selected from the group consisting of potassium iodide, sodium iodide, lithium iodide, and mixtures thereof.

11. The process according to claim 1 wherein the base is selected from the group consisting of potassium carbonate, sodium carbonate, cesium carbonate, potassium bicarbonate, sodium bicarbonate, sodium hydroxide, potassium hydroxide, and mixtures thereof.

12. The process according to claim 1 wherein the solvent is selected from the group consisting of methanol, toluene, ethyl acetate, acetonitrile, cyclohexane, dimethyl formamide (DMF), dimethylamine (DMA), dimethyl sulfoxide (DMSO), and mixtures thereof.

13. The process according to claim 1 wherein the reaction mixture comprising the compound of formula (II) and the compound of formula (III) is heatd to a temperature range of from 40-80° C.

14. The process according to claim 1 wherein the reaction mixture comprising the compound of formula (II) and the compound of formula (III) is heatd to a temperature range of from 62-68° C.

15. The process according to claim 1 wherein the process results in paliperidone in free base form.

16. The process according to claim 15 wherein the free base is converted to a pharmaceutically acceptable salt thereof.

17. The process according to claim 16 wherein the salt is an acid addition salt formed by treatment with a hydrohalic acid.

18. The process according to claim 16 wherein the salt is an acid addition salt formed by treatment with an acid selected from the group consisting of hydrochloric acid, hydrobrornic acid, sulfuric acid, nitric acid, phosphoric acid, acetic acid, propanoic acid, hydroxyacetic acid, 2-hydroxypropanoic acid, 2-oxopropanoic acid, ethanedioic acid, propanedioic acid, butanedioic acid, (Z)-2-butenedioic acid, (E)-2-butenedioic acid, 2-hydroxybutanedioic acid, 2,3-dihydroxybutanedioic acid, 2-hydroxy-1,2,3-propanetricarboxylic acid, methanesulfonic acid, ethanesulfonic acid, benzenesulfonic acid, 4-methylbenzenesulfonic acid, cyclohexanesulfamic acid, 2-hydroxybenzoic acid or 4-amino-2-hydroxybenzoic acid.

19. The process according to claim 1 comprising further purification, wherein the purification comprises:

(I) dissolving the paliperidone prepared according to claim 1 in a chlorinated solvent;
(ii) concentrating the solution; and
(iii) isolating the paliperidone using a suitable solvent.

20. The process according to claim 19 wherein the chlorinated solvent used in step (i) is selected from the group consisting of methylene chloride, ethyene chloride, chloroform, or mixtures thereof.

21. The process according to claim 19 wherein the chlorinated solvent in step (i) is mixed with a second solvent, wherein the second solvent is selected from the group consisting of methanol, isopropyl alcohol, acetone, methyl isobutyl ketone, ethyl acetate, isopropyl acetate, toluene and acetonitrile, or mixtures thereof.

22. The process according to claim 19 wherein the suitable solvent used in step (iii) is selected from the group consisting of acetone, methanol, ethyl acetate, isopropyl alcohol, methyl isobutyl ketone (MIBK), acetonitrile, isopropyl acetate, toluene or mixtures thereof.

23. The process according to claim 1 wherein the paliperidone or pharmaceutically acceptable salt thereof has keto impurity of 0.06% or less.

24. The process according to claim 1 wherein the paliperidone or pharmaceutically acceptable salt thereof has a keto impurity of 0.02% or less.

25. The process according to claim 1 wherein the paliperidone or pharmaceutically acceptable salt thereof has a keto impurity of 0.06% or less observed at 25° C. after 12 months.

26. The process according to claim 1 wherein the paliperidone or pharmaceutically acceptable salt thereof has a total impurity level of 0.22% or less.

27. The process according to claim 1 wherein the paliperidone or pharmaceutically acceptable salt thereof has a total impurity level of 0.18% or less.

28. The process according to claim 1 wherein the paliperidone or pharmaceutically acceptable salt thereof has a total impurity level of 0.22% or less observed at 40° C. after 6 months.

29. The process according to claim 1 wherein the inhibiting agent is present in an amount of 0.01 to 0.2 moles per 1 mole of compound of formula (II).

30. The process of claim 1, wherein the mixture comprising the compound of formula (II) and the compound of formula (III) is heated to a temperature of from about 63° C. to about 67° C.

31. The process of claim 1, wherein heating the mixture comprising the compound of formula (II) and the compound of formula (III) causes the compound of formula (II) and the compound of formula (III) to react.

* * * * *

UNITED STATES PATENT AND TRADEMARK OFFICE
CERTIFICATE OF CORRECTION

| | | |
|---|---|---|
| PATENT NO. | : 9,062,049 B2 | Page 1 of 1 |
| APPLICATION NO. | : 14/122108 | |
| DATED | : June 23, 2015 | |
| INVENTOR(S) | : Ravikumar Puppala et al. | |

It is certified that error appears in the above-identified patent and that said Letters Patent is hereby corrected as shown below:

In the Claims:

Column 15, Claim 13, Line 25, replace "is heatd to" with --is heated to--.
Column 15, Claim 14, Line 29, replace "is heatd to" with --is heated to--.
Column 15, Claim 18, Line 39, replace "hydrobrornic" with --hydrobromic--.
Column 16, Claim 20, Line 7, replace "ethyene" with --ethylene--.

Signed and Sealed this
Twenty-seventh Day of October, 2015

Michelle K. Lee
*Director of the United States Patent and Trademark Office*